(12) United States Patent
Kocur

(10) Patent No.: US 7,022,132 B2
(45) Date of Patent: *Apr. 4, 2006

(54) STENTS WITH TEMPORARY RETAINING BANDS

(75) Inventor: Gordon J. Kocur, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 224 days.

This patent is subject to a terminal disclaimer.

(21) Appl. No.: 10/084,765

(22) Filed: Feb. 26, 2002

(65) Prior Publication Data

US 2002/0116050 A1    Aug. 22, 2002

Related U.S. Application Data

(63) Continuation of application No. 09/232,404, filed on Jan. 15, 1999, now Pat. No. 6,350,277.

(51) Int. Cl.
*A61F 11/00*    (2006.01)

(52) U.S. Cl. .................................................. 623/1.11

(58) Field of Classification Search .............. 623/1.32, 623/1.38, 1.23, 1.12, 1.15, 1.11; 606/194, 606/195; 156/196
See application file for complete search history.

(56) References Cited

U.S. PATENT DOCUMENTS

| | | | |
|---|---|---|---|
| 3,105,492 A | 10/1963 | Jeckel | 128/334 |
| 3,272,204 A | 9/1966 | Artandi et al. | 128/334 |
| 3,304,557 A | 2/1967 | Polansky | 3/1 |
| 3,463,158 A | 8/1969 | Schmitt et al. | 128/334 |
| 3,479,670 A | 11/1969 | Medell | 3/1 |
| 3,878,565 A | 4/1975 | Sauvage | 3/1 |
| 3,993,078 A | 11/1976 | Bergentz et al. | 128/334 |
| 4,610,688 A | 9/1986 | Silvestrini et al. | 623/1 |
| 4,655,771 A | 4/1987 | Wallsten | 623/1 |
| 4,731,073 A | 3/1988 | Robinson | 623/1 |
| 4,743,251 A | 5/1988 | Barra | 623/1 |
| 4,954,126 A | 9/1990 | Wallsten | 600/36 |
| 5,061,275 A | 10/1991 | Wallsten et al. | 623/1 |
| 5,064,435 A | 11/1991 | Porter | 623/12 |
| 5,123,917 A | 6/1992 | Lee | 623/1 |
| 5,192,307 A | 3/1993 | Wall | 623/1 |
| 5,234,457 A | 8/1993 | Andersen | 606/198 |
| 5,330,500 A | 7/1994 | Song | 606/198 |
| 5,383,926 A | 1/1995 | Lock et al. | 623/1 |
| 5,405,377 A * | 4/1995 | Cragg | 623/1 |
| 5,405,378 A | 4/1995 | Strecker | 623/1 |
| 5,433,723 A * | 7/1995 | Lindenberg et al. | 623/1 |
| 5,445,646 A * | 8/1995 | Euteneuer et al. | 606/198 |
| 5,476,508 A | 12/1995 | Amstrup | 623/1 |
| 5,534,007 A | 7/1996 | St. Germain et al. | 606/108 |
| 5,556,413 A * | 9/1996 | Lam | 623/1 |
| 5,571,135 A | 11/1996 | Fraser et al. | 606/198 |
| 5,632,840 A * | 5/1997 | Campbell | 156/196 |

(Continued)

FOREIGN PATENT DOCUMENTS

EP    0 382 014 A1    1/1990

(Continued)

*Primary Examiner*—Carey E. O'Connor
(74) *Attorney, Agent, or Firm*—Vidas, Arrett & Steinkraus

(57) ABSTRACT

A self-expanding stent is formed of a stent framework and retaining segments disposed about the framework. The retaining segments hold the stent in a partially or fully contracted state in a bodily vessel. The retaining segments are constructed to fail after a predetermined time or upon the application of a predetermined force. Upon failure of the segments, the stent expands in the bodily vessel.

16 Claims, 11 Drawing Sheets

U.S. PATENT DOCUMENTS

| | | | |
|---|---|---|---|
| 5,670,161 A * | 9/1997 | Healy et al. | 604/8 |
| 5,779,732 A * | 7/1998 | Amundson | 623/1.15 |
| 5,830,217 A | 11/1998 | Ryan | 606/108 |
| RE35,988 E | 12/1998 | Winston et al. | 623/1 |
| 5,843,158 A | 12/1998 | Lenker et al. | 623/1 |
| 5,849,037 A | 12/1998 | Frid | 623/1 |
| 5,871,537 A * | 2/1999 | Holman et al. | 623/1 |
| 5,873,906 A * | 2/1999 | Lau et al. | 623/1 |
| 5,873,907 A * | 2/1999 | Frantzen | 623/1.11 |
| 5,899,935 A * | 5/1999 | Ding | 623/1.53 |
| 5,957,975 A * | 9/1999 | Lafont et al. | 623/1 |
| 5,972,029 A | 10/1999 | Fuisz | 623/1 |
| 5,989,280 A * | 11/1999 | Euteneuer et al. | 606/198 |
| 6,350,277 B1 | 2/2002 | Kocur | |
| 6,432,130 B1 * | 8/2002 | Hanson | 623/1.11 |

FOREIGN PATENT DOCUMENTS

| | | |
|---|---|---|
| WO | 88/00813 | 11/1988 |
| WO | 98/11846 | 3/1998 |

* cited by examiner

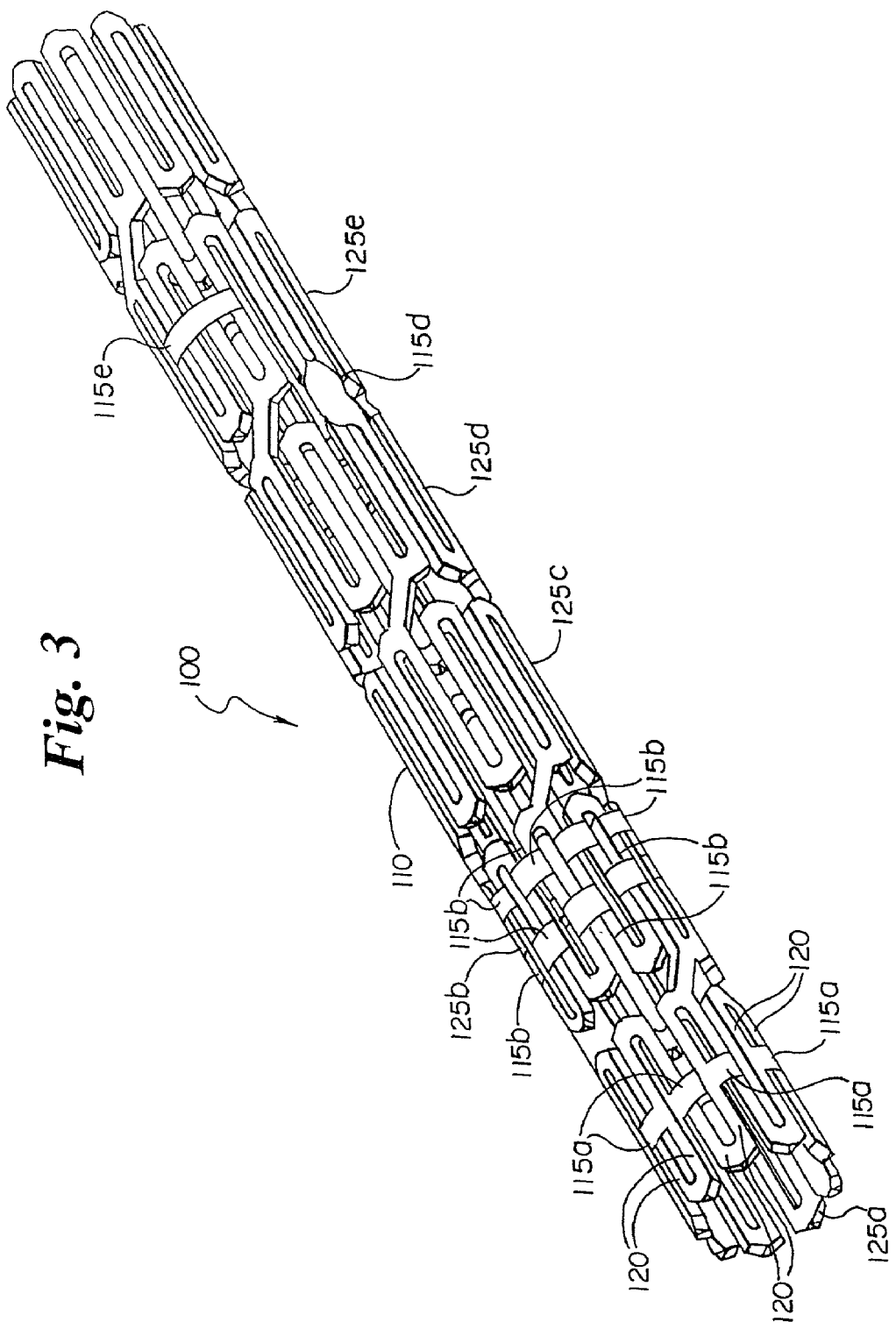

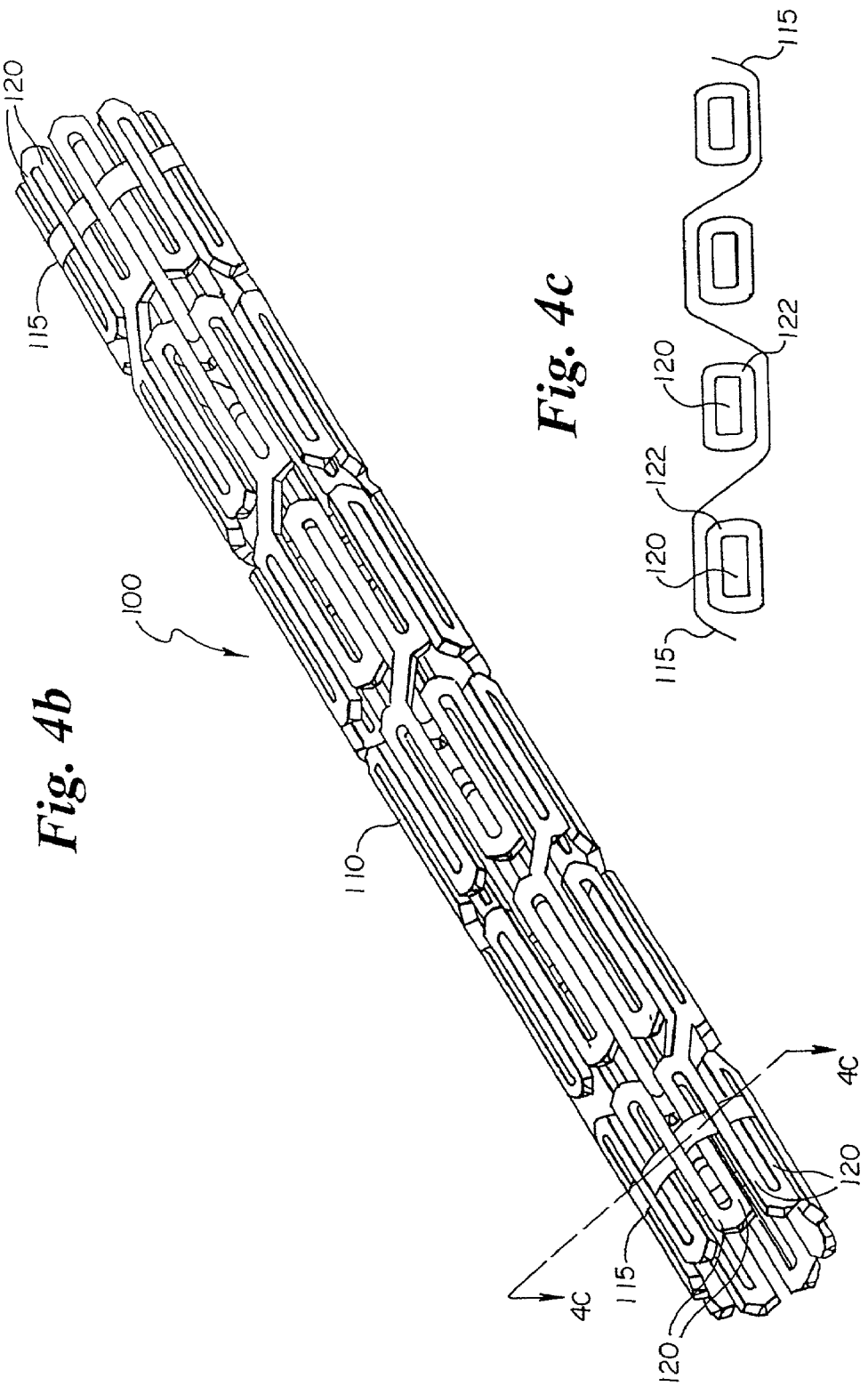

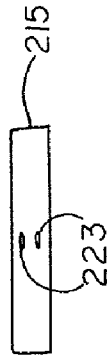
*Fig. 5a*
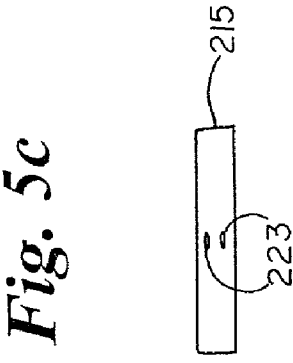
*Fig. 5b*
*Fig. 5c*
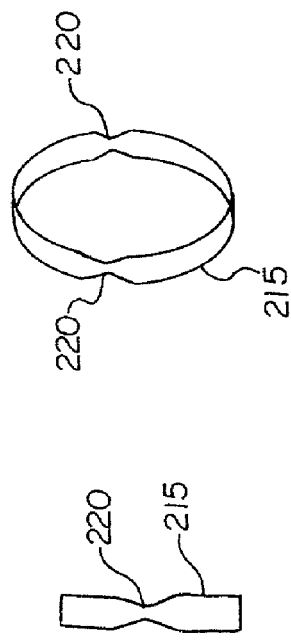
*Fig. 6a*
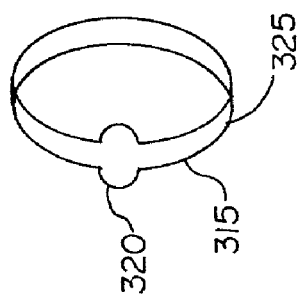
*Fig. 6b*
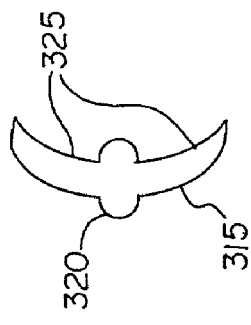
*Fig. 6c*

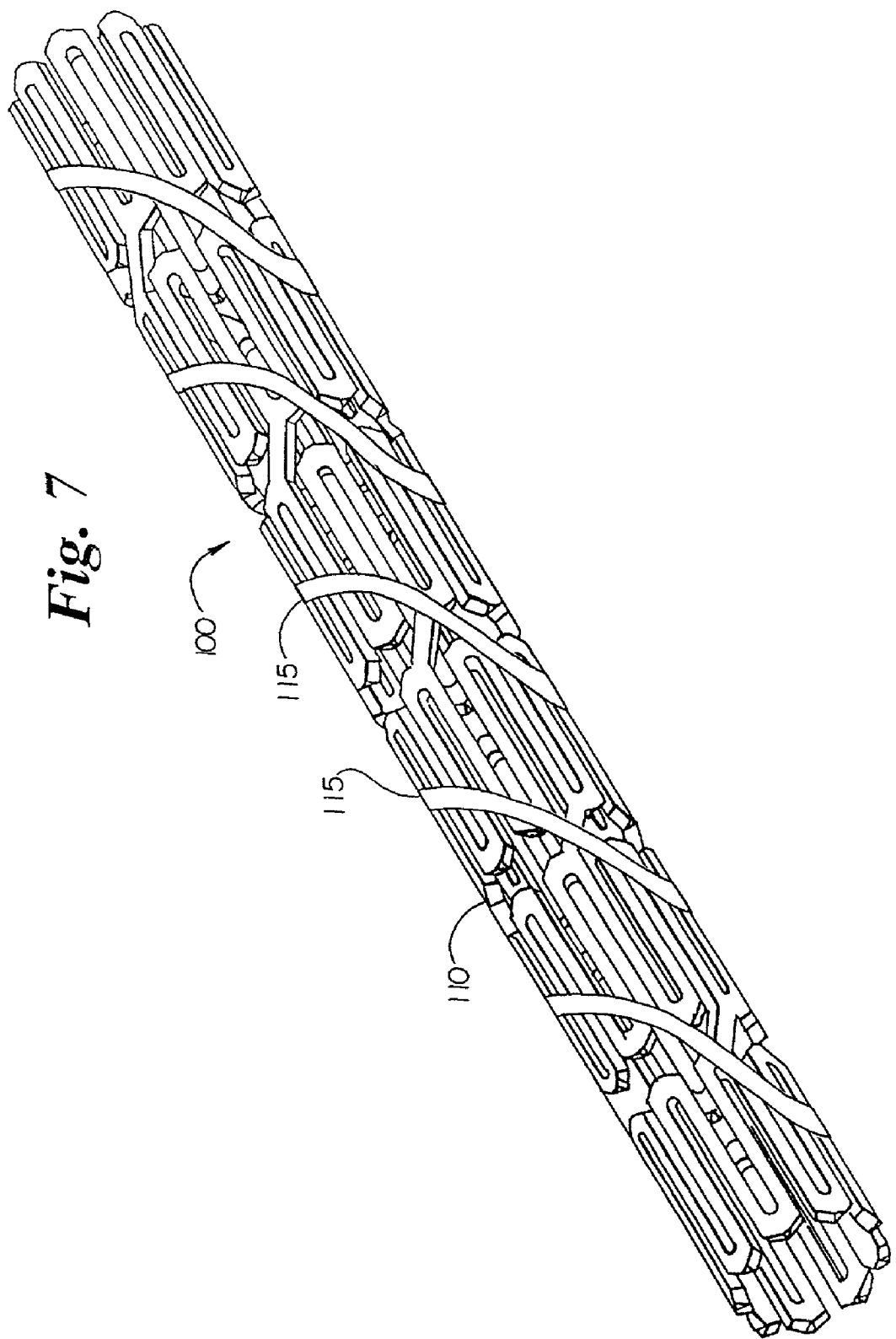

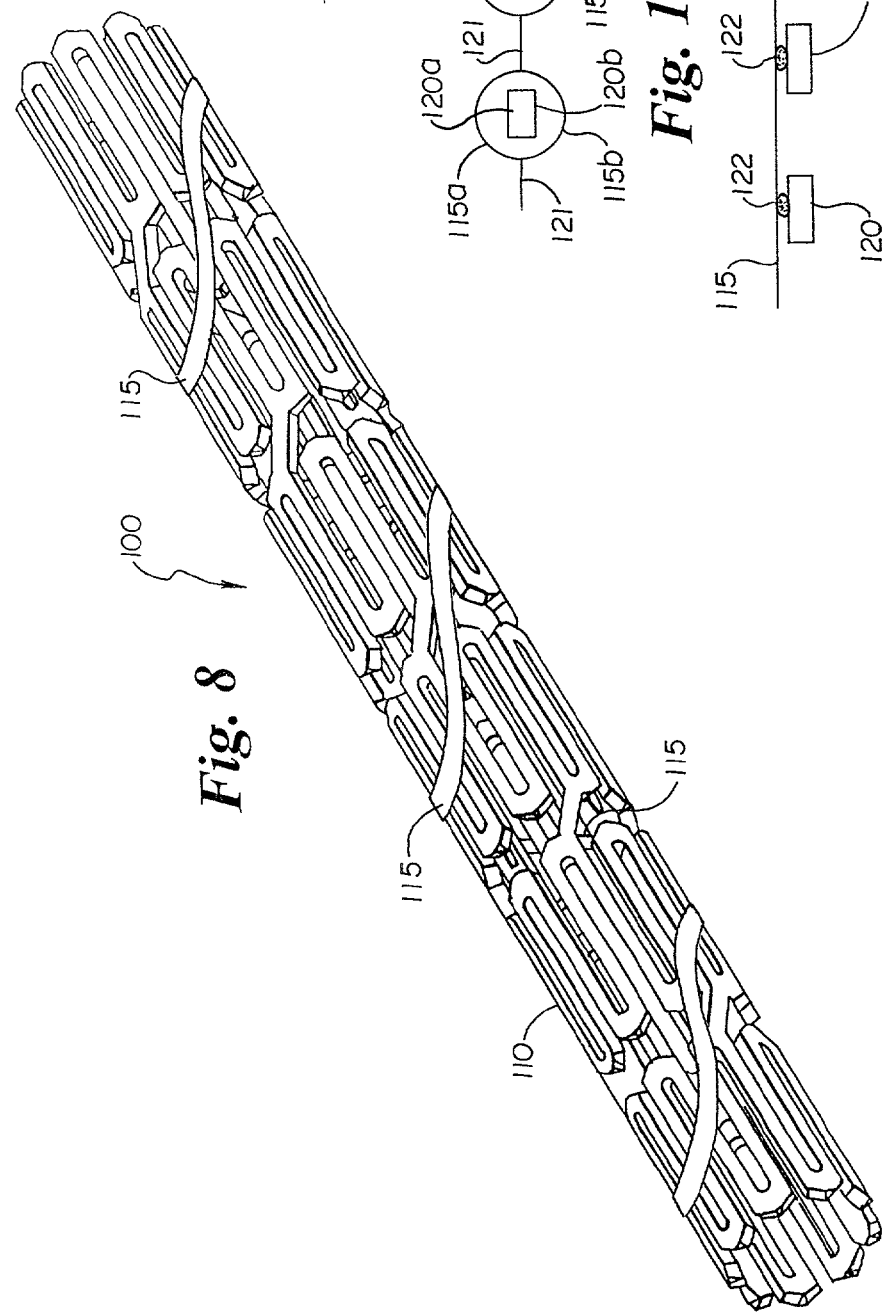

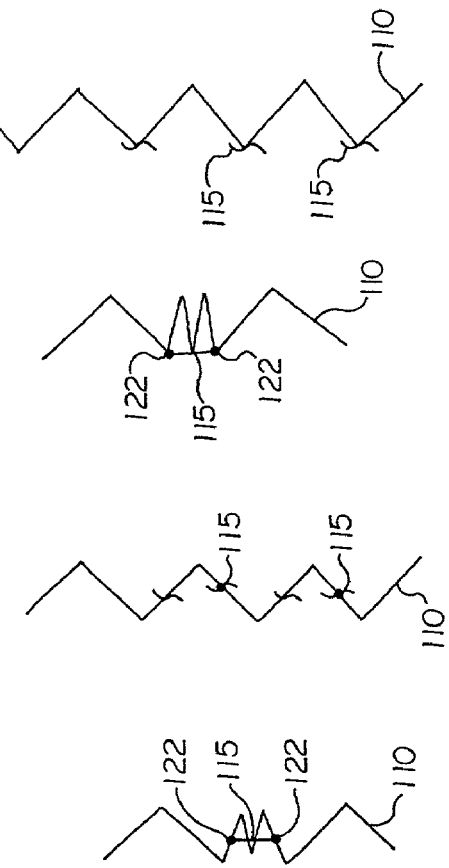
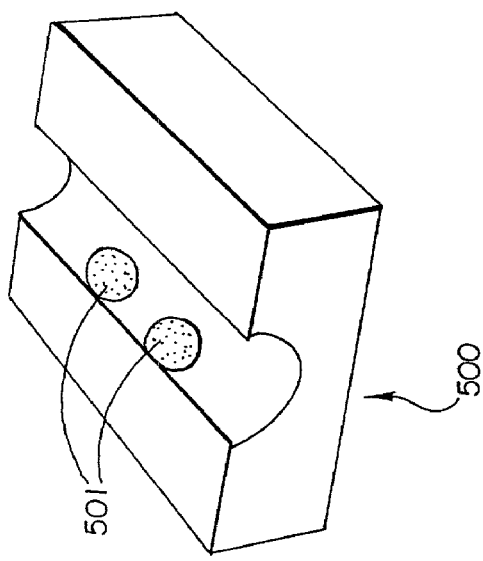

STENTS WITH TEMPORARY RETAINING BANDS

CROSS-REFERENCE TO RELATED APPLICATIONS

This application is a Continuation application of application Ser. No. 09/232,404, filed Jan. 15, 1999 now U.S. Pat. No. 6,350,277 issued Aug. 31, 2004, the entire contents of which are hereby incorporated by reference

BACKGROUND OF THE INVENTION

This invention relates specifically to stents but also generally to any expandable, implantable endoprosthesis such as grafts, stent-grafts and the like. When the term 'stent' is used herein, it is to be understood in a general sense as including all such expandable prostheses, unless otherwise indicated.

The use of endoprostheses such as stents, stent-grafts and grafts is well known in maintaining the patency of bodily vessels including blood vessels and biliary ducts. Typically, an endoprosthesis is implanted in a vessel which has been occluded, which is subject to an aneurysm, which has a lesion present or is otherwise damaged. Often, during the implantation of the endoprosthesis, the vessel will suffer from trauma. The trauma may be as a result of the dilation prior to the implantation of the endoprosthesis, the presence of a foreign body (the endoprosthesis) in the bodily vessel or as a result of other causes. Regardless of the source of the trauma, the vessel may be in a weakened and inflamed state as a result of implantation of the endoprosthesis. Although it is desirable to maintain the vessel at as large a diameter as possible to minimize the possibility of restenosis, the weakening of the vessel resulting from the trauma limits the extent to which the vessel can be dilated.

The endoprostheses that are currently available are typically balloon expandable, self-expanding, or balloon assisted self-expanding devices. Balloon expandable stents achieve their maximum diameter upon expansion by a balloon. Once they have been seated in the vessel, they are incapable of further expansion unless a balloon is reinserted in the stent and expanded. Self-expanding and balloon assisted expandable stents, on the other hand, continually exert an outward force as they try to attain their maximum possible diameter. Thus, even after the stent is implanted, if it has not reached its maximum diameter it continues to try to open further exerting a force on the vessel walls.

It would be desirable to provide an endoprosthesis which has some of the characteristics of balloon expandable stents following deployment and which has some of the properties of self-expanding stents after a predetermined period of time or after the application of a predetermined amount of force thereto. In particular, it is desirable to provide an endoprosthesis which does not impart to the vessel walls the outward forces associated with a self-expanding stent while the vessel is recovering from the trauma of the deployment procedure and yet provides the outward expanding force of a self-expanding stent when the vessel is sufficiently recovered from the trauma.

It is also desirable to provide an endoprosthesis which only partially expands or does not expand at all during deployment and which expands at some later point following deployment.

The present invention provides such an endoprosthesis.

For the purposes of this disclosure, unless otherwise indicated, the term 'degradation' shall refer to degradation in its ordinary sense as well as biodegradation, erosion, and dissolution.

BRIEF SUMMARY OF THE INVENTION

The invention is directed to an expandable stent comprising an expandable stent framework which is expandable from a reduced diameter configuration to a fully expanded configuration. At least one stent retaining segment which is constructed to fail is disposed about the stent framework to maintain the stent framework in a reduced diameter state until the retaining segment fails. The retaining segment may be constructed to fail after a predetermined period of time has elapsed and/or after a predetermined amount of force has been applied to the stent. The retaining segment may be entirely biodegradable, biodegradable in part, erodible or made of an inert material with fatigue points.

In one embodiment of the invention, the retaining segment forms a band around the outside of the stent or interwoven about the stent. In particular, the retaining segment may be woven such that it alternates on the inner and outer strut surfaces.

The retaining segment may also be provided in the form of a web.

The invention is also directed to treatment methods in which the inventive stent is deployed and further expands upon failure of the retaining segments. In the case of an inert segment, failure of the retaining segment may result from mechanical failure. Stresses on the stent which are likely to result in or contribute to the desired failure include pulsing blood pressure which is thought to cause an alternating lengthening and shortening of the stent.

In the case of a biodegradable segment or an erodible segment, failure results from degradation or erosion of the segment. Finally, in the case of a segment made of inert material and connecting dots of biodegradable material, failure results from degradation or erosion of the connecting dots.

More generally, the invention is directed to the application of a secondary increased expansive force to a body lumen by an implantable expandable medical device such as a stent endoprostheses including stents, stent-grafts, grafts and vena cava filters at a predetermined time following implantation into a body lumen.

BRIEF DESCRIPTION OF THE SEVERAL VIEWS OF THE DRAWING(S)

FIG. 3 shows a perspective view of an inventive stent illustrating several types of retaining segments.

FIG. 4b shows a perspective view of another inventive stent.

FIG. 4c shows a cross-sectional view of the stent of FIG. 4b along the lines 4c—4c.

FIGS. 5a–c show retaining segments with fatigue points.

FIG. 6a shows a perspective view of a retaining segment.

FIG. 6b shows a perspective view of another retaining segment.

FIG. 6c shows a perspective view of another retaining segment.

FIG. 7 shows a perspective view of another embodiment of the inventive stent.

FIG. 8 shows a perspective view of another embodiment of the inventive stent.

FIG. 9 shows a partial cross-section of a stent with a retaining segment fused to the stent.

FIG. 10 shows a partial cross-section of a stent with a retaining segment bonded the stent.

FIGS. 11a–e are schematic representations of stent with retaining segments in the form of webs.

FIG. 12 is a perspective view of a die for use in the present invention.

FIGS. 13a–d are schematic representations of a stent with a retaining band prior to (FIGS. 13a and 13c) and following (FIGS. 13b and 13d) failure of the retaining segment.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
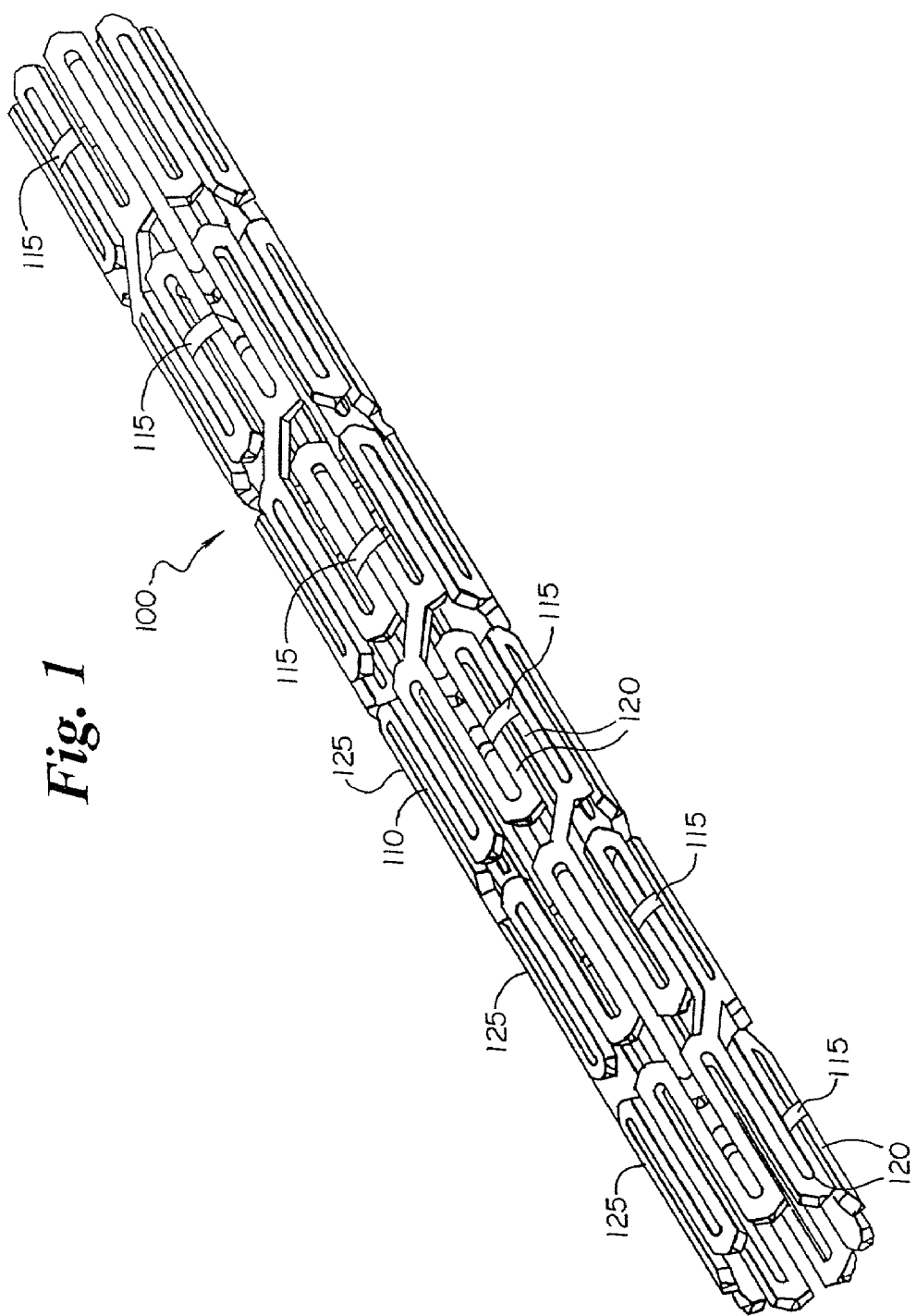
FIG. 1 shows a perspective view of an inventive stent.

With reference to the Figures in general and FIG. 1 in particular, the present invention is directed to an expandable stent, shown generally at 100, comprising an expandable stent framework 110, and a stent retaining segments 115 which are selected portions of the stent framework. Expandable stent framework 110 is a self-expanding stent which is expandable from a reduced diameter configuration to a fully expanded configuration. Stent retaining segments 115 maintains the stent framework in a less than fully expanded configuration until it fails. In the embodiment of FIG. 1, one pair of struts 120 per stent section 125 are joined together with a retaining segment 115. Each stent retaining segment 115 is circumferentially offset from the adjacent stent retaining segment by one strut 120.

Figure 2:
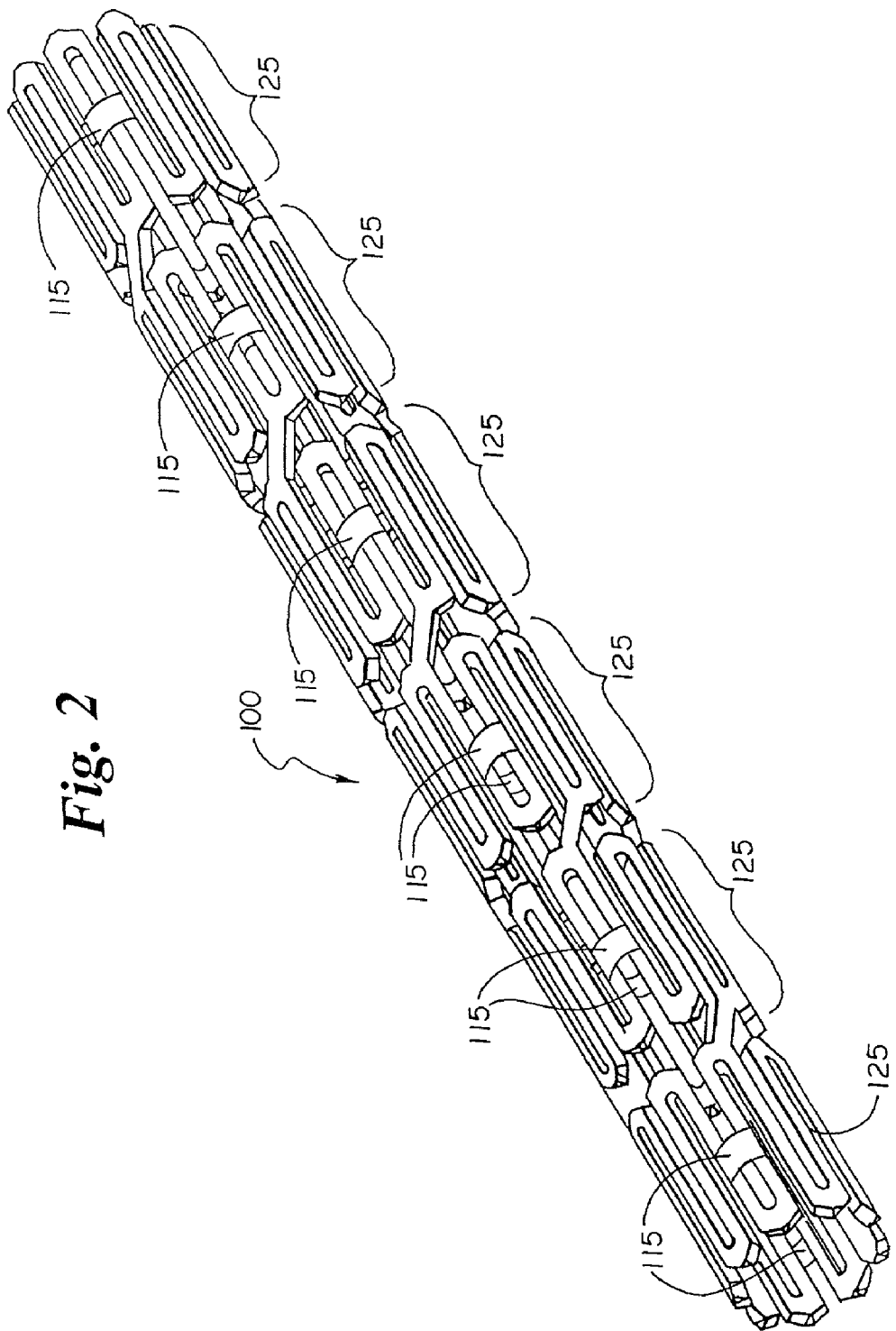
FIG. 2 shows a perspective view of another inventive stent.

The invention also contemplates providing a plurality of stent retaining segments per stent section. FIG. 2 shows stent 100 with two stent retaining segments 115 per stent section 125. Stent retaining segments 115 are oppositely disposed from one another across stent section 125.

FIG. 3 illustrates several other configurations of stent retaining segments. In stent section 125a, stent retaining segments 115a join every other pair of adjacent struts 120 in the center of the struts. In stent section 125b, every pair of adjacent struts are joined by stent retaining segments 115b. Stent retaining segments 115b are seen to alternate between a first end of adjacent and a second end of adjacent struts. The stent of FIG. 3 also shows a retaining segment 115d connecting adjacent stent sections 125d and 125e. The stent of FIG. 3 also shows a retaining segment 115e extending between three adjacent struts. It is understood that the stent of FIG. 3 is intended to be illustrative of several embodiments. Those of ordinary skill in the art will recognize that the invention contemplates stents in which a desired number of stent sections have stent retaining segments as in section 125a. Similarly, the invention contemplates stents having stent retaining segments arranged entirely as in section 125b. It will also be recognized that the invention contemplates stents with interconnected stent sections as in sections 125d and 125e. Finally, it will be recognized that each retaining segment may restrain multiple struts beyond the two shown in the figure.

The use of small retaining segments is beneficial for several reasons. First, retaining individual segments of the stent allows for greater stent flexibility. Second, using relatively small retaining segments results in a reduced negative tissue response to the implant and the segment in particular. Third, retaining only stent segments allows for better control over stent expansion and thus, how the additional secondary force is applied to the body lumen.

Figure 4A:
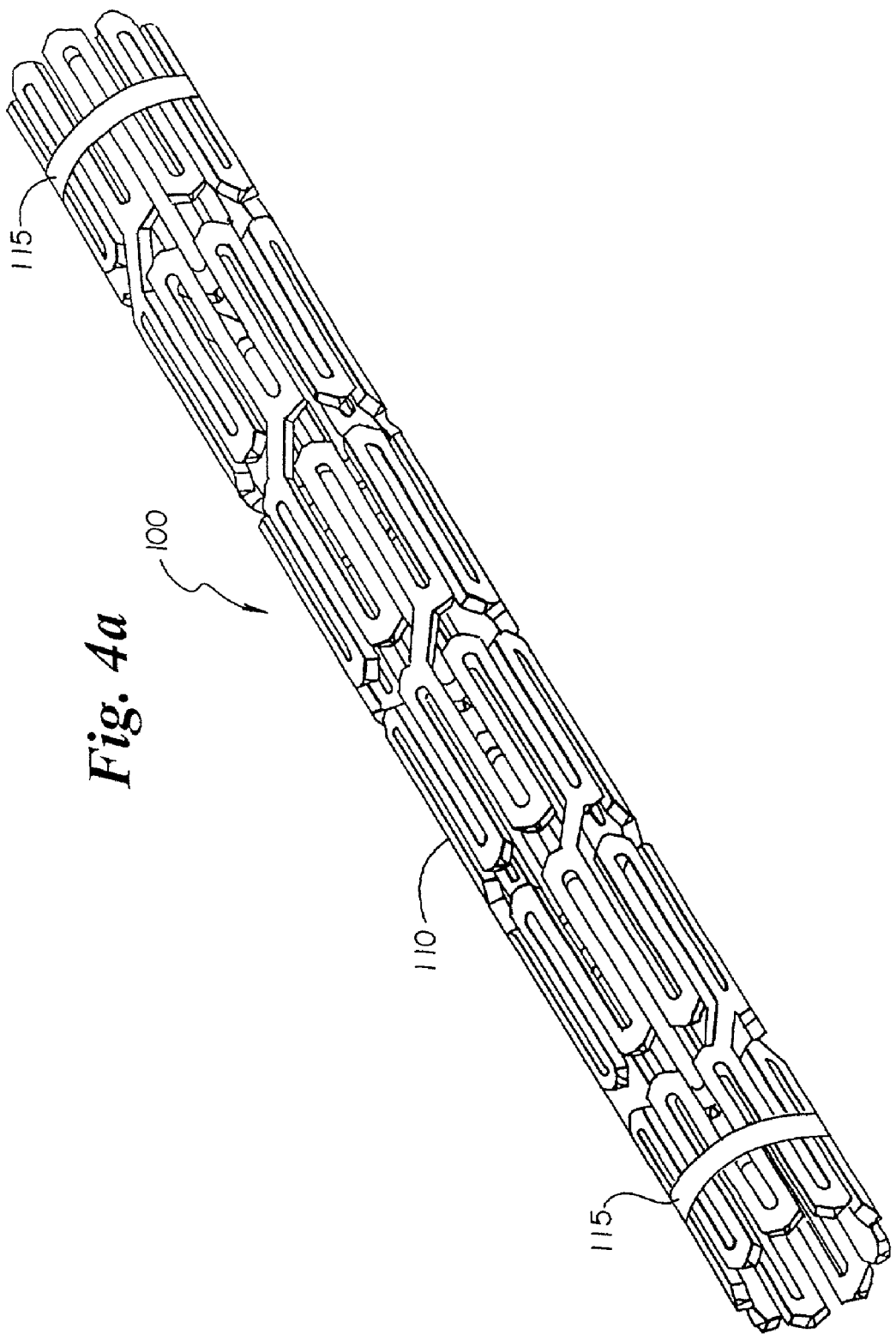
FIG. 4a shows a perspective view of another inventive stent.

The invention also contemplates the use of larger stent retaining segments in the form of stent retaining bands. In one embodiment of the invention, the stent retaining segments form one or more bands extending around the circumference. The stent of FIG. 4a, shown generally at 100, comprises an expandable stent framework 110, and a stent retaining segment 115 which is disposed about the circumference of the stent 110 in the form of a band. Expandable stent framework 110 is a self-expanding stent which is expandable from a reduced diameter configuration to a fully expanded configuration. Stent retaining segment 115 maintains the stent framework in a less than fully expanded configuration until it fails. The invention also contemplates the possibility of providing the stent with additional retaining bands beyond the two shown in FIG. 4a.

The band-like segments may extend around the stent from the outside of the stent or may be interwoven around the circumference of the stent as shown in FIGS. 4b and 4c. Bands 115 weave in-between struts 120.

The invention contemplates several different types of stent retaining segments. One stent retaining segment suitable for use in the present invention is shown in FIG. 5a. Stent retaining segment 215 has a single fatigue point 220. Fatigue point 220 is a narrowed region of the band. FIG. 5b shows a stent retaining band 215 with two fatigue points 220. The shape of the fatigue points shown in FIGS. 5a and 5b is intended to be for illustrative purpose only. Fatigue points of other geometries and configurations may also be used. A retaining band with a single fatigue point may also be used as may a retaining band with additional fatigue points. FIG. 5c shows a retaining segment 215 with two holes 223 punched therethrough. Fewer or additional holes may also be present in the region to weaken the segment.

Retaining band 215 is made of an inert or biostable material such as polytetrafluoroethylene (PTFE). Other inert or biostable materials may also be used. Desirably, a material with a low tissue response such as PTFE, polyurethanes, polyesters, and silicones will be used.

Another suitable stent retaining segment is shown generally at 315 in FIG. 6a. Retaining segment 315 is formed of two segments of inert or biostable material 325 and a segment of biodegradable material 320 joined together. Such a design may also be used for a stent retaining band as shown in FIG. 6b. Retaining band 315 is formed of a segment of inert or biostable material 325 and a segment of biodegradable material 320 joined together. As shown in FIGS. 6a and 6b, biodegradable segment 320 is provided in the form of a dot. Biodegradable segment 320 may suitably be provided in other shapes as well. In particular, the retaining segment or band may be provided with the same general shape as bands 215 shown in FIGS. 5a and 5b, with the fatigue point replaced by a biodegradable segment where the band narrows. An embodiment of retaining band 315 having two inert segments 325 and two biodegradable segments 320 is shown in FIG. 6c. A retaining segment may be similarly prepared with multiple biodegradable segments. The invention further contemplates the use of additional inert segments and additional biodegradable segments.

Another embodiment of the invention is shown in FIG. 7. Stent 100 comprises an expandable stent framework 110, and a stent retaining band 115 which is disposed about the stent the circumference of the stent 110. Expandable stent framework 110 is a self-expanding stent which can expand from a reduced diameter configuration to a fully expanded configuration. Stent retaining band 115 is disposed about stent framework 110 at an oblique angle relative to the longitudinal axis 130 of the stent. The invention is not intended to be limited to the specific oblique angle shown but rather, is intended to encompass the full range of oblique angles. The stent may have fewer or more retaining bands than shown in FIG. 7.

Another embodiment is shown in FIG. 8. Stent 100 is retained in a reduced diameter configuration via stent retaining band 115 which is helically disposed about the stent.

Figure 11A:
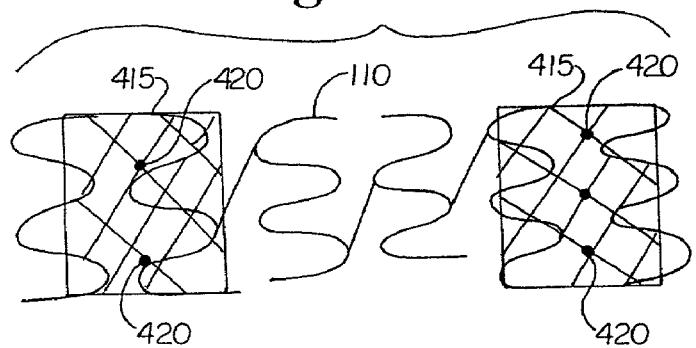
Figure 11B:
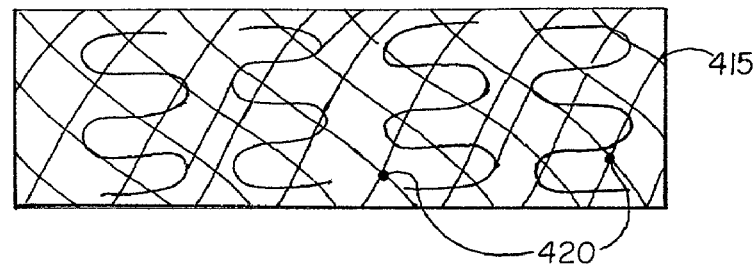

The invention also contemplates the use of retaining structures such as webs or nets to maintain the stent in a reduced configuration or less than fully expanded configuration. In general the web is of a woven or closed cell design that is fused to the exterior of the stent. The web can be in the shape of a tube that wraps around individual segments of the stent as shown generally at 415 in FIG. 11a. The web can also wraps around the entire length of the stent as shown in FIG. 11b. Web 415 is disposed about the length of stent framework 110. The web desirably has failure points 420 to allow the web to pull apart following failure.

Figure 11C:
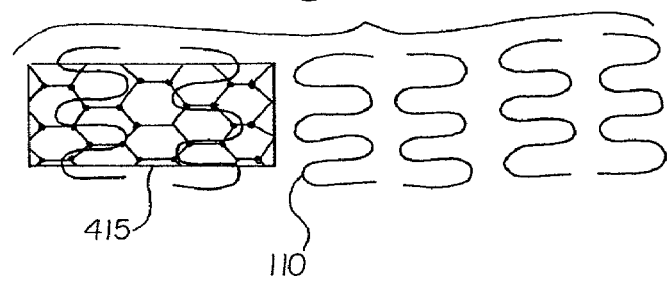
Figure 11D:
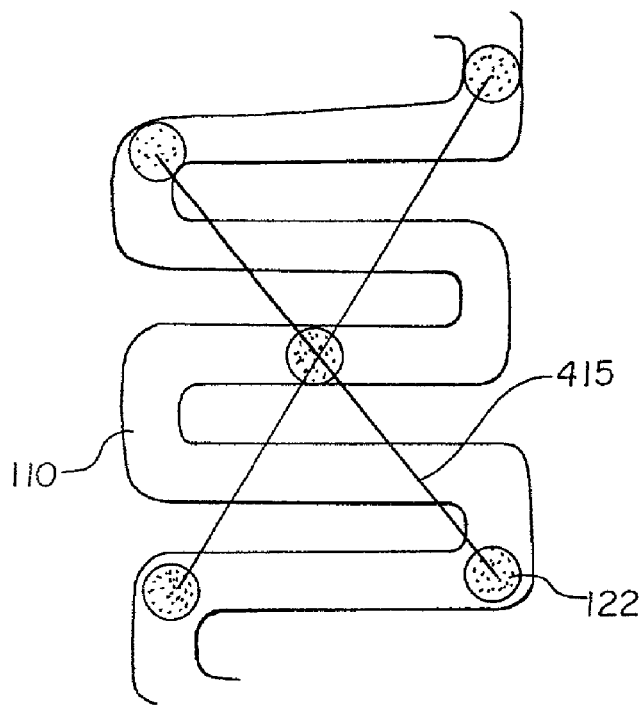

The web may also be a flat sheet as shown at 415 in FIG. 11c. Web 415 covers a group of cells like a patch. The web patch may either have failure points such as fatigue points or degradable portions to release the stent. The web patch may be attached to the stent struts via a degradable material as shown in FIG. 11d. Web 415 is attached to stent 110 via degradable adhesive 122.

Figure 11E:
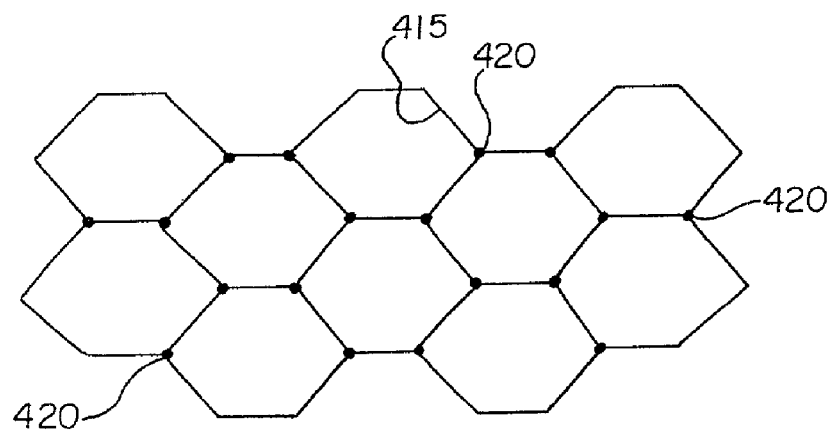

Another web configuration is shown at 415 in FIG. 11e. Web 415 is in a heaxgonal pattern with fatigue points 420 at the vertices of the hexagons. Other polygonal configuration may be substituted.

As with the retaining segments, the web may be made of a biodegradable material or may be made of an inert material with fatigue points. An inert material with biodegradable connecting material may also be used.

Although specific web configurations have been shown herein, those of ordinary skill in the art will understand these to be exemplary. Other web configurations may be used as well.

Retaining segments in the form of thin strips may be cut from sheets of a desired material. Threads of retaining segment may also be made by extrusion. Fatigue points may be made by varying the extrusion rate of the thread or by varying the tension on the thread during extrusion. Tension may also be used to introduce fatigue points into other types of retaining segments such as band-shaped retaining segments. Materials such as PTFE will neck under tension thereby forming a fatigue point. Fatigue points may also be placed in the material by cutting the material with a laser or with a punch as illustrated in FIG. 5c. Other methods for introducing fatigue points in a retaining segment include the spot application of a laser, of heat, of one or more solvents or other chemicals such as etchants, or of radiation to weaken or make the material brittle. Fatigue points may also be introduced into a retaining segment via the use of a second material in the segment.

As shown in some of the figures, the retaining segment is disposed on the outside of the stent. In situ, the retaining band is disposed between the vessel wall and the stent thereby facilitating encapsulation of the retaining band in tissue and preventing the inert material from being carried away in the vessel. This is particularly desirable where inert material is used for the retaining band.

The retaining segment may be secured to the stent in a variety of ways. Thread-like and other suitably sized retaining segments may be woven through the stent and/or tied to the stent or struts of the stent.

Alternatively, as illustrated in FIG. 9, a piece of retaining segment 115a may be placed on an outer surface of a strut 120a and another piece of retaining segment 115b may be placed on an inner surface of a strut 120b. The two pieces may then be fused together at 121 by heat, solvent, or adhesive.

Other methods of attachment include looping a retaining segment over a strut and securing the segment to itself or the strut melting with heat or solvent or adhesive. The retaining segment may also be wrapped around struts or layered around struts or attached directly to struts and secured thereto by applying heat or a solvent or other suitable adhesives including bioabsorbable, biodegradable or erodible compositions such as those disclosed below. As shown in FIGS. 4c and 10, a biostable material 122 may also be spot melted to or around a strut 120 and then fused to a retaining segment 115 made of biodegradable material by heat, solvent or adhesive. Where a solvent is used, excess solvent may be evaporated off or otherwise driven off.

One method of attachment involves providing a mandrel with degradable dots of material thereon. A stent is then disposed about the mandrel and a PTFE strip placed over a portion of the stent. Desired portions of the stent may be cliped so as to retain the stent in a reduced configuration on the mandrel. Heat is applied to the stent so as to fuse the dots to the stent and the PTFE. The stent is then cooled and removed from the mandrel.

In another method for applying a retaining segment to a stent, retaining segments are placed in a die which is then disposed about a stent in a reduced diameter configuration. The stent is then expanded. Specifically, a circular die at a desired intermediate stent diameter is provided. The die is provided in two halves, one of which is die, shown at 500 in FIG. 12, with groves 501 cut into the inner diameter surface for the retaining segment pattern. Retaining segments of a desired material are placed into the groves in the die halves and the die halves reassembled. A mandrel is provided and a nitinol stent is reduced in size onto the mandrel by cooling the stent below the austenitic-martensitic transition temperature to make it martensitic. Optionally, the mandrel may have grooves cut therein in the retaining segment pattern for placement of a desired material on inner diameter surface of stent. The reduced stent and mandrel are placed into the die. The stent is then heated to expand it inside the die. Adhesives, heat or solvent are then used to fuse the retaining segments to each other and/or the stent struts, retaining the stent at the desired diameter.

In yet another method of applying a retaining segment to a stent, clips may be used to hold struts or cells in the closed position in one or more desired portions of the stent. Threads of retaining segment material are laid across these portions of the stent and attached to the struts using adhesives, heat, or solvent.

Retaining segments may also be secured to a stent by hot extruding stands of material between confined struts (i.e. struts in a closed position or reduced diameter position).

Retaining segments may also be applied by first holding the stent in a desired reduced diameter configuration via the use of a retaining die or clamps. Strands of the retaining material may then be sprayed on the interior of the stent or the exterior of the stent in the area to be retained.

FIGS. 13a–13d illustrate a portion of a stent with a retaining segment prior to and after failure. As shown in FIGS. 13a and 13c, stent 110 has a retaining segment 115 which retains at least a portion of the stent in a reduced configuration. Segment 115 is attached to the stent at several points 122. Upon failure of the retaining segment 115, as shown in FIGS. 13b and 13d, stent 110 expands.

Suitable biodegradable or bioabsorbable materials for use in the retaining segments, bands or webs include:

Poly(L-actide) (PLLA), Poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) (PLA/PCL), poly(glycolide-co-caprolactone) (PGA/PCL), poly(phosphate ester), poly(DL-lactic acid), poly(glycolic acid).

PGA and PLLA/PGA are particularly desirable materials. Other suitable materials include collagen, fibrin, and cellulose.

More generally, general classes of degradable material include polyesters, polyamides, polyanhydrides and polyorthoesters. The latter two are surface erodible types. All of these are exemplary only.

As discussed above, the retaining segments may be designed to last for a predetermined period of time prior to failing. Where the retaining segment incorporates biodegradable materials, the lifetime of the segment may be altered by altering the chemical structure of the biodegradable portion of the segment. Hydrolysis is the basic reaction for the most biodegradable polymers. The hydrolytic degradation rate can be altered several thousand-fold by changing the chemical structure in the polymer backbone. For example, aliphatic polyanhydrides degrade in a few days while the aromatic polyanhydrides degrade over a period of a few years. Polyorthoester is a slow surface eroding material. In the presence of acid additive, a so-called excipient, it has a faster degradation rate. In contrast, in the presence of basic substance, it suppresses degradation. When longer lasting retaining segments are desired, the aromatic polyanhydride and non-additive polyorthoester will be preferred segment materials.

Also, for example, polymers that contain hydrolytically labile linkages in their backbone can hydrolyze by two different mechanisms. These are bulk erosion and surface erosion. In a bulk eroding polymer, the hydrolytic process occurs throughout the matrix of the polymer whereas in surface erosion the hydrolysis is only confined to the outer layer of the polymer. Thus, the latter is especially preferred when longer degradation is desired.

Specific segment materials include, for example, poly (ortho esters) such as 50:50 HD/t-CDM (1,6-Hexanediol-co-trans-Cyclohexanedimethanol) poly(ortho ester) with 0.2% poly(sebacic anhydride) excipient. Polyanhydrides such as poly[bis(p-carboxyphenoxy)propane anhydride] (PCPP) and poly(terephthalic anhydride) (PTA) may also be used.

If a polyanhydride is selected as the segment material, for example, its thickness can be selected such as to control degradation time. Thus, a segment may be tailored to have a degradation time of a week, a month, two months, or up to six months, or any other suitable period of time. Segment material of PGA, for example, may be provided at a selected thickness to provide a degradation period of about two weeks, for example.

The retaining segment is desirably designed to fail after a predetermined period of time following implantation in the bodily lumen. Failure includes mechanical failure and failure resulting from the biodegradation of at least a portion of the segment. Retaining segments which fail after about one week in the lumen are desirable as are retention segments that fail after about one month in the lumen. More desirably, the retention segments will last from about one to about six months following implantation. This allows the safe application of additional force to the body lumen after the initial tissue response to the implant and lumen remodeling has progressed or at a time were additional external force on the body lumen is expected to increase as in the case of an adjacent growing tumor.

The retaining segments may also be designed to fail after the application of a predetermined amount of force such as by a balloon.

The invention also contemplates providing the retaining segment with a treatment or therapeutic agent. A retaining segment material that elutes the therapeutic agent can be made by dissolving or suspending the therapeutic agent(s) and retaining segment polymer in a solvent. Threads may then be extruded and films may be sprayed or cast for making strips or webs for use as retaining segments. The treatment agent may also be provided by any other suitable techniques including impregnating or coating the segment with the treatment agent.

Desirable types of therapeutic agents include anti-inflammatory agents, anti-proliferative agents, anti-platelet agents, anti-thrombin agents, anti-oxidant agents, gene therapy agents and suitable combinations of the above agents. Suitable treatment agents include drugs such as radiochemicals to irradiate and prohibit tissue growth and human growth factors including VEGF (Vascular Endothelial Growth Factor), TGF-beta (Transforming Growth Factor-beta), IGF (Insulin—like Growth Factor), PDGF (Platelet—derived Growth Factor) and FGF (Fibroblast Growth Factor), etc. The drug can be an anticoagulant, e.g. D-Phe-ProArg chloromethyl ketone. An RGD (Arginine-Glycine-Aspartic Acid) peptide-containing compound, heparin, antithrombin compounds, platelet receptor antagonists, antibodies, aspirin, prostaglandin inhibitors, platelet inhibitors, or antiplatelet peptide may also be used. The drug can be an inhibitor of vascular cell growth, DNA, RNA, cholesterol-lowering agents, vasodilating agents. Other suitable drugs include Taxol™ (paclitaxel), 5-Fluorouracil, Beta-Estradiol. Metabolites and other derivatives of the above drugs or compounds may also be used. Any treatment agent may be used, singly or in combination.

The treatment agent may be impregnated into the retaining segments or may be provided as a coating on the segments. The treatment agent may be applied by immersing the segments in the treatment agent or spraying the agent onto the segments. Suitable techniques for applying the treatment agent may be found in U.S. application Ser. No. 08/874190 incorporated herein in its entirety by reference.

The invention is also directed to an expandable stent for implantation in a bodily lumen comprising an expandable stent framework and a stent retaining segment which is constructed to fail. As discussed above, the retaining segment may be designed to fail after a predetermined period of time such as about one week or about one month. The retaining segment may also be designed to fail upon the application thereto of a predetermined pressure such as that provided by a balloon.

The inventive stents, grafts and stent-grafts may be formed from any suitable self-expanding and balloon assisted self-expanding stent or graft known in the art. One such suitable self-expanding stent is disclosed in commonly assigned U.S. application Ser. No. 08/511076 filed Aug. 3, 1995, incorporated herein in its entirety by reference. Another suitable stent is the Wallstent stent, described in U.S. Pat. Nos. 4,655,771, 4,954,126 and 5,061,275 incorporated herein in their entirety by reference.

Suitable grafts may be formed by applying a graft material such as polytetrafluoroethylene (PTFE) or polyethylene terephthalate (PET) to the stent and securing it thereto by an appropriate means such as sutures. Other graft materials including polyurethane, collagen, silicone, polypropylene and polyolefin may also be used. The graft material may be used as inner liner for the stent or as an outer liner for the stent. Other types of self-expanding grafts may also be used in the practice of the invention.

The invention is intended to be used with self-expanding endoprostheses in general and as such is not limited to coronary endoprostheses. Non-coronary applications include biliary prostheses and ureteral prostheses. In particular, the inventive endoprostheses may prove useful where it is necessary to maintain the patency of vessels or ducts that are being closed by tumors including the bile duct and pancreatic tumors.

The invention provides endoprostheses which may partially expand or not expand at all during deployment and yet expand at a later point as a result of failure of a retaining segment.

In another aspect, the invention is directed to a treatment method which comprises the steps of implanting an expandable stent with retaining segments such as those disclosed above, in a bodily lumen. The retaining segments may be constructed to fail by biodegradation or erosion or mechanical failure after a predetermined period of time in the body such as about week or about a month. In accordance with this treatment method, the stent is implanted in a less than fully expanded state and expands upon the passage of a predetermined period of time such as a week, a month or longer with the failure or dissolution of the retaining segments. The stent may be delivered to the desired bodily location using a stent delivery catheter such as those disclosed in U.S. Pat. Nos. 5,534,007 and 5,571,135 incorporated herein in their entirety by reference or any other suitable stent delivery catheter.

Desirably, the retaining segments will be constructed to fail after the vessel has sufficiently healed to be able to safely withstand the increment in force following the failure of the segments.

The inventive treatment method also contemplates the deployment of a stent with retaining segments as disclosed above in a bodily lumen and the subsequent application of a predetermined force to the stent to more fully expand the stent. Additional force may be applied immediately after deployment of the stent as a 'touch-up' or after some suitable period of time following deployment (i.e. days, weeks or months). The additional force necessary to break the retention segments may be applied via an inflatable balloon on a catheter.

The invention is also directed more generally to an expandable medical device which is held in a contracted or partially contracted state by one or more retaining structures such as the segments described above. Suitable medical device include stents, stent-grafts, grafts and vena cava filters.

The above disclosure is intended to be illustrative and not exhaustive. This description will suggest many variations and alternatives to one of ordinary skill in this art. All these alternatives and variations are intended to be included within the scope of the attached claims. In particular, the invention contemplates stents with multiple types of retaining segments (e.g. bands and segments linking only several struts together). As such, stents which are combinations of those shown in the Figures are intended. Those familiar with the art may recognize other equivalents to the specific embodiments described herein which equivalents are also intended to be encompassed by the claims attached hereto.

What is claimed is:

1. An expandable stent comprising:
   an expandable stent framework, the stent framework expandable from a reduced diameter configuration to a fully expanded configuration;
   an at least one stent retaining segment interwoven about the stent, the at least one stent retaining segment having a coating thereon, the coating comprising at least one therapeutic agent, the stent retaining segment maintaining the stent framework in a less than fully expanded configuration, the stent retaining segment constructed and arranged to fail upon degradation of at least a portion of the segment.

2. The stent of claim 1 wherein, the stent retaining segment is further constructed and arranged to elute the at least one therapeutic agent upon degradation of the at least a portion of the segment.

3. The stent of claim 1 wherein the at least one therapeutic agent is selected from at least one member of the group consisting of: anti-inflammatory agents, anti-proliferative agents, anti-platelet agents, anti-thrombin agents, anti-oxidant agents, gene therapy agents, and combinations thereof.

4. The stent of claim 1 wherein the at least one therapeutic agent is selected from at least one member of the group consisting of: radiochemicals, human growth factors, anti-coagulants, RGD (Arginine-Glycine-Aspartic Acid) peptide-containing compounds, heparin, antithrombin compounds, platelet receptor antagonists, antibodies, aspirin, prostaglandin inhibitors, platelet inhibitors, antiplatelet peptides, vascular cell growth inhibitors, DNA, RNA, cholesterol-lowering agents, vasodilating agents, TaxolJ (paclitaxel), 5-Fluorouracil, Beta-Estradiol, metabolites, and any combinations thereof.

5. A covering for covering at least a portion of a stent, the covering comprising:
   a tubular section of biodegradable material for covering an unexpanded stent wherein such tubular section is dimensioned so as to constrain the expansion of the stent, the tubular section attached to the stern with a biostable material, at least a portion of the tubular section having a coating thereon, the coating comprising at least one therapeutic agent.

6. The covering of claim 5 wherein, the at least a portion of the tubular section is constructed and arranged to elute the at least one therapeutic agent.

7. The covering of claim 5 wherein the at least one therapeutic agent is selected from at least one member of the group consisting of: anti-inflammatory agents, anti-proliferative agents, anti-platelet agents, anti-thrombin agents, anti-oxidant agents, gene therapy agents, and combinations thereof.

8. The covering of claim 5 wherein the at least one therapeutic agent is selected from at least one member of the group consisting of: radiochemicals, human growth factors, anticoagulants, RGD (Arginine-Glycine-Aspartic Acid) peptide-containing compounds, heparin, antithrombin compounds, platelet receptor antagonists, antibodies, aspirin, prostaglandin inhibitors, platelet inhibitors, antiplatelet peptides, vascular cell growth inhibitors, DNA, RNA, cholesterol-lowering agents, vasodilating agents, TaxolJ (paclitaxel), 5-Fluorouracil, Beta-Estradiol, metabolites, and any combinations thereof.

9. A covering for covering at least a portion of a stent, the covering comprising:
a tubular section of polymeric material for covering an unexpanded stent wherein such tubular section is dimensioned so as to constrain the expansion of the stent, the tubular section comprised of at least one band, the at least one band having a single line of perforations at which the band comes apart to modify the expansion characteristics of the section and thereby constrain the expansion of the underlying stent, at least a portion of the tubular section comprising at least one therapeutic agent.

10. The covering of claim 9 wherein, the at least a portion of the tubular section is constructed and arranged to elute the at least one therapeutic-agent.

11. The covering of claim 9 wherein the at least one therapeutic agent is selected from at least one member of the group consisting of anti-inflammatory agents, anti-proliferative agents, anti-platelet agents, anti-thrombin agents, anti-oxidant agents, gene therapy agents, and combinations thereof.

12. The covering of claim 9 wherein the at least one therapeutic agent is selected from at least one member of the group consisting of: radiochemicals, human growth factors, anticoagulants, RGD (Arginine-Glycine-Aspartic Acid) peptide-containing compounds, heparin, antithrombin compounds, platelet receptor antagonists, antibodies, aspirin, prostaglandin inhibitors, platelet inhibitors, antiplatelet peptides, vascular cell growth inhibitors, DNA, RNA, cholesterol-lowering agents, vasodilating agents, TaxolJ (paclitaxel), 5-Fluorouracil, Beta-Estradiol, metabolites, and any combinations thereof.

13. A covering for covering at least a portion of a stent, the covering comprising:
a tubular section of bio-stable material for covering an unexpanded stent wherein such tubular section is dimensioned so as to constrain the expansion of the stent, the tabular section comprised of at least one band, the at least one band being of a helical construction, a pattern of perforations provided in the tubular section selected to modify the expansion characteristics of the section and thereby constrain the expansion of the underlying stent, at least a portion of the tubular section comprising at least one therapeutic agent.

14. The covering of claim 13 wherein, the at least a portion of the tubular section is constructed and arranged to elute the at least one therapeutic-agent.

15. The covering of claim 13 wherein the at least one therapeutic agent is selected from at least one member of the group consisting of: anti-inflammatory agents. anti-proliferative agents, anti-platelet agents, anti-thrombin agents, anti-oxidant agents, gene therapy agents, and combinations thereof.

16. The covering of claim 13 wherein the at least one therapeutic agent is selected from at least one member of the group consisting of: radiochemicals, human growth factors, anticoagulants, RGD (Arginine-Glycine-Aspartic Acid) peptide-containing compounds, heparin, antithrombin compounds, platelet receptor antagonists, antibodies aspirin, prostaglandin, inhibitors, platelet inhibitors, antiplatelet peptides, vascular cell growth inhibitors, DNA, RNA, cholesterol-lowering agents, vasodilating agents, TaxolJ (paclitaxel), 5-Fluorouracil, Beta-Estradiol, metabolites, and any combinations thereof.

\* \* \* \* \*